(12) United States Patent
Olsen (10) Patent No.: US 8,679,095 B2
(45) Date of Patent: Mar. 25, 2014

(54) REGULATOR

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/570,698

(22) Filed: Aug. 9, 2012

(65) Prior Publication Data

US 2012/0303000 A1    Nov. 29, 2012

Related U.S. Application Data

(62) Division of application No. 10/862,768, filed on Jun. 7, 2004, now Pat. No. 8,251,981.

(51) Int. Cl.
*A61K 9/22*    (2006.01)

(52) U.S. Cl.
USPC ..................................... 604/891.1

(58) Field of Classification Search
USPC ............... 604/141, 890.1–892.1; 137/501
See application file for complete search history.

*Primary Examiner* — Melanie Hand (57) ABSTRACT

A flow regulator (19, 208, 308, 408) may be used in a drug delivery system 10. The regulator includes a chamber that is divided by a diaphragm (111, 211, 311, 411) into a first and second subchamber. A third subchamber is in fluid communication with the first subchamber. A valve (26, 217, 317, 417) is operatively connected to the diaphragm, wherein pressure differences between the first subchamber and second subchamber result in movement of the diaphragm and movement of the diaphragm controls operation of the valve. A flow restrictor (116, 216, 316, 416) is in fluid communication between the first and second subchambers. Flow of a drug (11, 101) is thereby regulated.

19 Claims, 8 Drawing Sheets

REGULATOR

CROSS-REFERENCE TO RELATED APPLICATIONS

The present application is a divisional of U.S. patent application Ser. No. 10/862,768, filed Jun. 7, 2004, now allowed, which application is hereby incorporated by reference as if re-written in its entirety.

FIELD OF THE INVENTION

This invention relates generally to the delivery of drugs from an implantable drug delivery device and more particularly to a regulator and a regulator in combination with other components for controlling the flow rate of the drugs.

BACKGROUND OF THE INVENTION

Previously, there have been many developments in the implantable drug delivery art. For instance, U.S. Pat. No. 4,594,058 discloses a single valve diaphragm pump that includes a pump housing, a flexible diaphragm reciprocally movable in the pump housing, and a filter means, and an outlet valve. The pump was designed to provide a stroke volume that is constant over various ranges of ambient pressure and reservoir pressure.

U.S. Pat. Nos. 5,067,943 and 5,088,983 discloses another plantable pump system which utilizes a flow regulator that isolates the regulator sensing chamber from the flow of the drug. The regulator uses either an independent sensing chamber or is coupled to a propellant chamber of the pump. Further, a downstream restrictor may be used to provide additional pressure drop between the regulator and the outlet chamber.

BRIEF SUMMARY OF THE INVENTION

In a first embodiment, the invention is a pump mechanism for use in an implantable drug delivery system having a positive pressure reservoir. The pump mechanism has a pump having a pump inlet and a pump outlet. A pressure regulator includes a housing having a chamber. A diaphragm divides the chamber into a first subchamber and a second subchamber. The first subchamber has a first inlet and a first outlet and the second subchamber has a second inlet and a second outlet. A valve is provided for controlling flow through the first inlet, the valve is operatively connected to the diaphragm. The diaphragm is moveable within the chamber and responds to difference in pressure between the first subchamber and the second subchamber. The pump inlet is in fluid communication with the first outlet and the pump outlet is in fluid communication with the second inlet.

In another embodiment, the invention is a drug delivery system for implantation in a body for delivery of a liquid drug. The system includes a housing having a chamber. A diaphragm divides the chamber into a first subchamber in a first flow path and a second subchamber in a second flow path. The diaphragm is moveable in response to differences in pressure between the first subchamber and the second subchamber to regulate pressure difference between the first flow path and the second flow path. A valve is operably linked with the diaphragm to open the first flow path when pressure in the second flow path exceeds pressure in the first flow path by a predetermined amount. A pump has an inlet in fluid communication with the first flow path and an outlet in fluid communication with the second flow path. An infusion pump housing defines a drug reservoir. A propellant chamber is within the pump housing and proximate the drug reservoir, wherein pressure is exerted on the drug reservoir. The drug reservoir has a reservoir inlet for receiving the liquid drug and a reservoir outlet, the outlet in fluid communication with the first flow path, whereby the liquid drug is delivered independent of changes in reservoir pressure and ambient pressure.

In another embodiment, the invention is an inflatable flow regulator for use with a drug delivery system. The flow regulator includes a chamber and a diaphragm dividing the chamber into a first subchamber and a second subchamber. A third subchamber is in fluid communication with the first subchamber through a first inlet. A valve is operably connected to the diaphragm, the valve for controlling flow from the third subchamber to the first subchamber through the first inlet, wherein pressure differences between the first subchamber and the second subchamber result in movement of the diaphragm and movement of the diaphragm controls operation of the valve. The first subchamber has a first outlet and the second subchamber has a second inlet and a second outlet. A flow restrictor has an end in fluid communication with the first outlet and a second end in fluid communication with the second outlet, wherein flow of a drug from a drug delivery system to the second outlet is regulated.

In another embodiment, the invention is a drug delivery system for implantation in a body for delivery of a liquid drug. The system includes a chamber and a diaphragm dividing the chamber into a first subchamber and a second subchamber. A third subchamber is in fluid communication with the first subchamber through a first inlet. A valve is operably connected to the diaphragm. The valve controls flow from the third subchamber to the first subchamber through the first inlet, wherein pressure differences between the first subchamber and the second subchamber result in movement of the diaphragm and movement of the diaphragm controls operation of the valve. The first subchamber has a first inlet and the second subchamber has a second inlet and a second outlet. The infusion pump housing defines a drug reservoir. A propellant chamber is within the pump housing and proximate the drug reservoir, wherein pressure is exerted on the drug reservoir. The drug reservoir has a reservoir inlet for receiving a drug in a reservoir outlet. The reservoir outlet is in fluid communication with the first inlet of the first subchamber. A flow restrictor has a first end in fluid communication with the first outlet and a second end in fluid communication with the second outlet, wherein flow of a drug from a drug delivery system through the second outlet is regulated.

In another embodiment, the invention is an implantable flow regulator and flow restrictor combination for use with a drug delivery system. The system includes a chamber and a diaphragm dividing the chamber into a first subchamber and a second subchamber. A third subchamber is in fluid communication with the first subchamber through a first inlet. A valve is operatively connected to the diaphragm. The valve controls flow from the third subchamber to the first subchamber through the first inlet, wherein pressure differences between the first subchamber and the second subchamber result in movement of the diaphragm and movement of the diaphragm controls operation of the valve. The first subchamber has a first outlet and the second subchamber has a second inlet and a second outlet. The chamber has an outer surface. A flow restrictor comprising a spiral groove is operatively connected to the outer surface and an outer cylinder is positioned over the spiral groove, wherein a capillary is formed by the groove and outer cylinder.

DETAILED DESCRIPTION OF THE INVENTION

The regulators of the present invention utilize three chambers. One is an inlet chamber, another is a control chamber, and another is the outlet chamber. However, in some embodiments as will be described more fully hereafter, the inlet chamber may be a portion of the drug reservoir. There is a normally closed valve between the inlet chamber and the control chamber. When used in this application, "normally closed" means that increasing the pressure in the inlet chamber tends to force the valve closed rather than force it open. The valve opens when the pressure in the control chamber is less than the pressure in the outlet chamber or conversely, when the pressure in the outlet chamber is greater than the pressure in the control chamber. "Normally closed" does not mean that the valve is closed, just that the valve tends to open when the pressure in the control chamber is less than in the outlet chamber, if, in the description, a valve is actually open or closed, the description will be given without reference to the term "normally".

Figure 1:
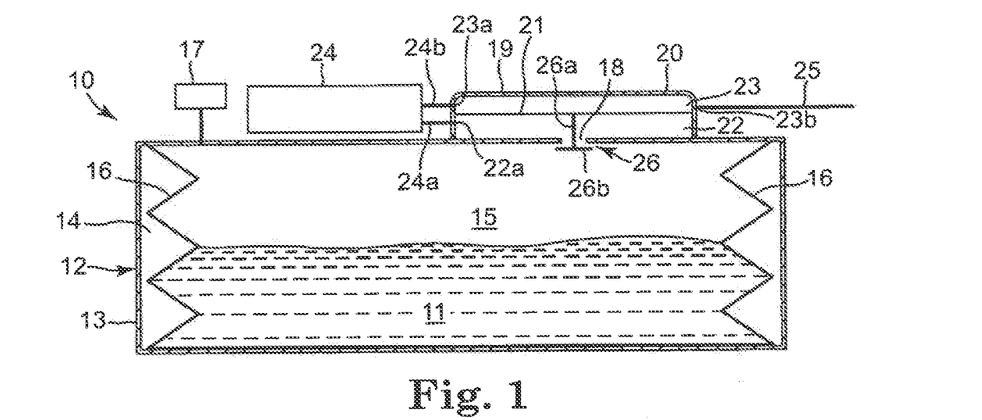
FIG. 1 shows a first embodiment of a drug delivery system in accordance with the present invention.

Referring now to the figures, wherein like numerals represent like parts throughout the several views, there is generally disclosed at 10 a drug delivery system. The drug delivery system 10 is for implanting in a body for delivery of a liquid drug 11. The drug delivery system 10 includes a drug reservoir 12 that includes a housing 13 that is divided into two chambers. The first chamber 14 is a propellant chamber and the second chamber 15 is the drug reservoir chamber. A metal bellows 16 divides the housing 13 into the two chambers 14, 15. A refill septum 17 is in fluid communication with the drug reservoir chamber 15 and allows for subcutaneous refilling of the drug reservoir chamber 15 with a drug 11. The drug reservoir chamber 15 has an opening 18. A regulator 19 is operatively connected to the housing 13. The regulator 19 includes a housing 20. A flexible diaphragm 21 divides the chamber inside of the housing 20 into two subchambers. The first subchamber is control chamber 22 and the second subchamber is outlet chamber 23. The diaphragm 21 may be any suitable flexible diaphragm and may be constructed from any suitable material such as silicone or titanium. A pump 24 has an inlet 24a and an outlet 24b. The inlet 24a is in fluid communication with the control chamber 22 through an outlet 22a of the outlet chamber 22. The pump outlet 24b is in fluid communication with the outlet chamber 23 through inlet 23a of the outlet chamber 23. Further, the outlet chamber 23 has an outlet 23b that is in fluid communication with a suitable outside device such as a catheter 25. A valve 26 is shown having a valve stem 26a and a sealing member 26b operatively connected to the stem 26a. As shown in FIG. 1, the valve 26 is connected to the diaphragm 21. The valve 26 is positioned in the opening 18. The opening 18 provides a passageway to place the drug reservoir 15 in fluid communication with the regulator 19. Alternately, the valve would not necessarily have to be connected, by suitable means such as welding, to the diaphragm and may be held in a closed position by a spring as shown in FIG. 3. In any event, the valve is operatively connected to the diaphragm, i.e., the movement of the diaphragm 21 will cause movement of the valve 26. As previously indicated, the valve 26 is normally closed. Further, without a pressure difference between the control chamber and outlet chamber, the valve 26 is in a closed position. When there is sufficient pressure differential, the valve 26 moves to an open position, as shown in FIG. 1, and will be described more fully hereafter. The amount of pressure differential required to open the valve 26 is dependent upon the diaphragm 21 stiffness plus the initial position of the valve relative to the diaphragm. In addition, there may be a biasing spring stiffness, if a spring is used as shown in FIG. 2.

In operation, the drug 11 is delivered to the drug reservoir chamber 15 through the refill septum 17. While the valve 26 is normally closed, it is also held in a closed position because of the initial bias of the diaphragm 21. This may also be adjusted by the biasing spring as shown in FIG. 2 or the spring as shown in FIG. 3. When the pump 24 is actuated, the drug 11 is taken in through the inlet 24a and dispensed through the outlet 24b into the outlet chamber 23 and catheter 25. This lowers the pressure in the control chamber 22 (at the inlet for the pump 24). After one or more actuations, the pressure in the control chamber 22 drops slowly enough to cause the valve 26 to open slightly (as shown in FIG. 1) which allows the drug 11 to flow into the control chamber 22. The decrease in pressure in the control chamber 22 allows for the diaphragm 21 to deflect downward, thereby moving the valve 26. When the valve 26 is opened, as shown in FIG. 1, and the drug 11 flows into the control chamber 22, the pressure in the control chamber 22 will increase, causing the diaphragm 21 to move upward, thereby urging the valve 26 back towards a closed position. The drug 11 is maintained in the control chamber 22 for future pump activation by the slow leakage by the valve due to the pressure differential across the diaphragm 21. If the pump 24 is run at a high rate, the pressure will drop slightly lower in the control chamber 22 in order to force the valve 26 further open to accommodate the increased flow of the drug 11 through the valve opening 18.

Figure 2:
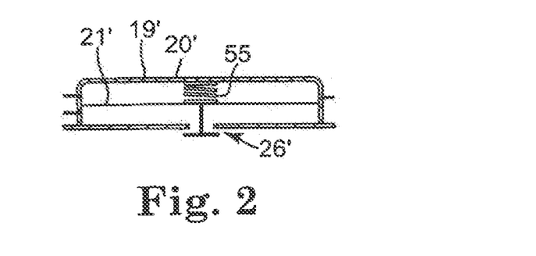
FIG. 2 shows another embodiment of a regulator for use in the drug delivery system shown in FIG. 1 with a biasing spring.
Figure 3:
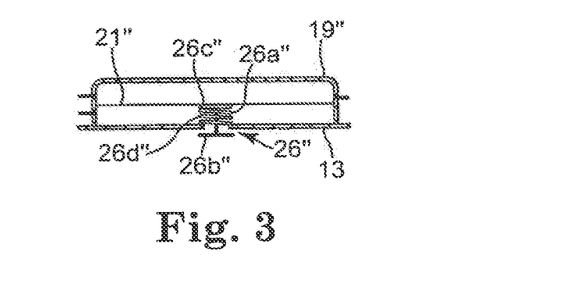
FIG. 3 is another embodiment of a regulator for use in the drug delivery system shown in FIG. 1 with a spring to hold the valve closed.

Referring now to FIGS. 2 and 3, there are further embodiments of a regulator that may be utilized in the drug delivery system, such as that shown in FIG. 1. The regulator 19', shown in FIG. 2, is similar to the regulator 19 shown in FIG. 11. However, regulator 19' has the addition of a spring 55. The spring 55 is positioned between the housing 20' and the diaphragm 21'. The spring 55 is just one method of setting the pressure difference that is needed to open the valve 26'. Referring now to FIG. 3, there is a regulator 19". Again, this regulator 19" is similar to regulator 19 and only the differences will be discussed in detail.

The valve 26" includes a valve stem 26a" and a sealing member 26b" operatively connected to a stern 26a. A C-clip 26c", or other suitable fastening device is secured to the valve stem 26a" and a spring 26d" is positioned between the C-clip 26c" and the housing 13. The valve 26 in FIG. 1 is typically welded to the diaphragm. By the construction shown in FIG. 3, the spring 26d" can hold the valve 26 in a closed position without the valve stem 26a" being welded to the diaphragm 21".

Figures 4, 5:
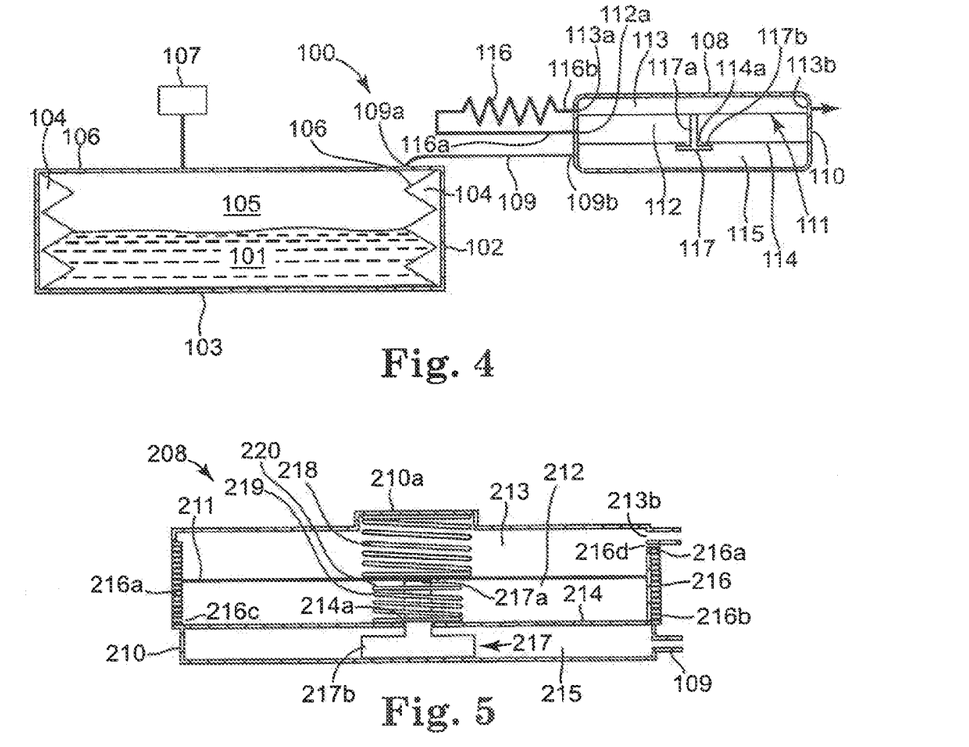
FIG. 4 shows a another embodiment of a drug delivery system in accordance with the present invention.
FIG. 5 shows another embodiment of a regulator for use in the drug delivery system shown in FIG. 4.

Referring now to FIG. 4, there is disclosed a drug delivery system generally designated as 100. The drug delivery system 100 is for implanting in a body for delivery of a liquid drug 101. The drug delivery system 100 includes a drug reservoir 102 that includes a housing 103 that is divided into two chambers. The first chamber 104 is a propellant chamber and the second chamber 105 is a reservoir chamber. A metal bellows 106 divides the housing 103 into the two chambers 104, 105. A refill septum 107 is in fluid communication with the drug reservoir chamber 105 and allows for subcutaneous refilling of the drug reservoir chamber 105 with a drug 101. A regulator 108 is in fluid communication with the drug reservoir 102. As shown in FIG. 4, a line 109 places the reservoir 102 in fluid communication with the regulator 108. In this application, a "line" is any fluid passageway. The line 109 has a first end 109a that is operatively connected to an outlet opening in the drug reservoir chamber 105 and a second end 109b in fluid communication an opening in the regulator 108. However, it is understood that the regulator may also be positioned proximate the drug reservoir 102 and appropriately constructed so that the outlet from the drug reservoir chamber is in fluid communication with the regulator 108 without the necessity of a line, somewhat similar to that shown in FIG. 1. The regulator 108 includes a housing 110. A flexible diaphragm 111 divides the chamber inside of the housing 110 into a first subchamber 112, which is a control chamber and a second subchamber 113 which is an outlet chamber. The diaphragm 111 may be any suitable flexible diaphragm and may be constructed from any suitable material such as silicone or titanium. A wall 114 further divides the chamber of the housing 110 into a third subchamber 115, an inlet chamber. The wall 114 has an opening 114a formed therein. A flow restrictor 116 is placed in fluid communication between the first subchamber 112 and second subchamber 113. The first end 116a is in fluid communication with an outlet 112a of subchamber 112 and a second end 116b is in fluid communication with an inlet 113a of the second subchamber 113. The opening 114a is both an outlet for the third subchamber 115 and an inlet for the first subchamber 112. An outlet 113b of the second subchamber 113 is adapted and configured to be in communication with a suitable outside device such as a catheter. A valve 117 is shown having a valve stem 117a and a sealing member 117b operatively connected to the stem 117a. As shown in FIG. 4, the valve 117 is connected to the diaphragm 111. The valve 117 is positioned in the opening 114a. The opening 114a provides a passageway to place subchamber 115 in fluid communication with subchamber 113. Alternately, the valve would not necessarily have to be connected to the diaphragm and may be held in a closed position similar to that shown with respect to the embodiment shown in FIG. 3. In any event, the valve is operatively connected to the diaphragm 111, i.e., the movement of the diaphragm 111 will cause movement of the valve 117. As previously indicated, the valve 117 is normally closed. Further, without a pressure difference between the control chamber and the outlet chamber, the valve 117 is adjusted so that it is in an open position, as shown in FIG. 4. It should be noted that this is the opposite as discussed with respect to the valve 26 as used in the drug delivery system 10 shown in FIG. 1. The valve 117 stays open until the pressure in the first subchamber 112 exceeds the pressure in the second subchamber 113 by a predetermined amount. For example, the valve 117 may be set to close when the control chamber or first subchamber 112 pressure is 2.0 psi greater than the second subchamber 113. At 2.0 psi, there will be a flow through the flow restrictor defined by the Hagen Poisielle laminar flow equations. The valve 117 will stabilize in a partially open position. If the valve 117 allows more than the desired amount of drug 105 to pass, then the pressure drop across the flow restrictor 116 will increase, and this pressure change will tend to close the valve 117. If the valve 117 were to allow less than the desired amount of drugs 105 to pass, then the pressure across the flow restrictor 116 will decrease, and the valve 117 will tend to open. This self-correcting phenomena will tend to keep the valve 117 position and flow rate at the desired amount. This flow rate is maintained independent of temperature, altitude, bellows position or catheter resistance.

Referring now to FIG. 5, there is shown another regulator 208 for use in the drug delivery system shown in FIG. 4. A regulator that is utilized with respect to the drug delivery system shown in FIG. 4 may have a spring which tends to close the valve. Further, the diaphragm may have a biasing spring to set the initial height open-close pressure. If the force exerted by either of the springs were adjusted during operation, the flow rate through the system could be adjusted, and hence the flow rate could be controlled via electronics or telemetry. Such regulators are shown in FIGS. 5 and 6.

Figure 8:
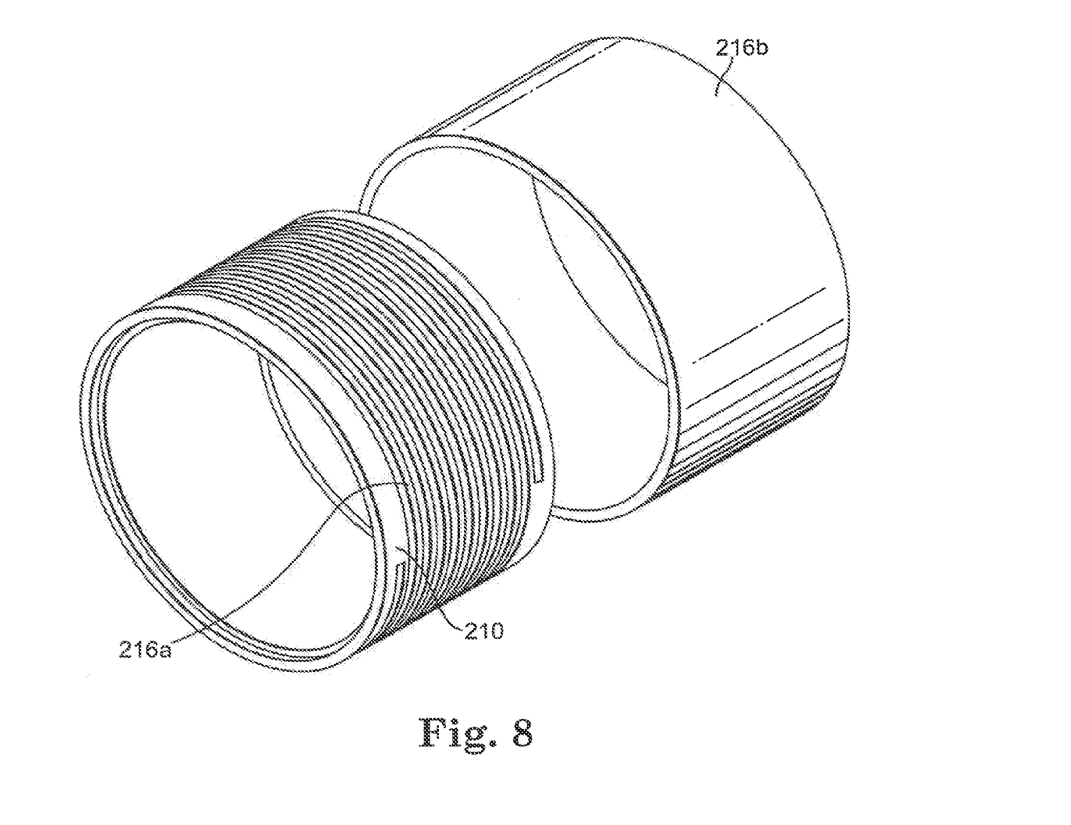
FIG. 8 is an exploded perspective view shown in more detail the combination of a flow restrictor and regulator.
Figure 9:
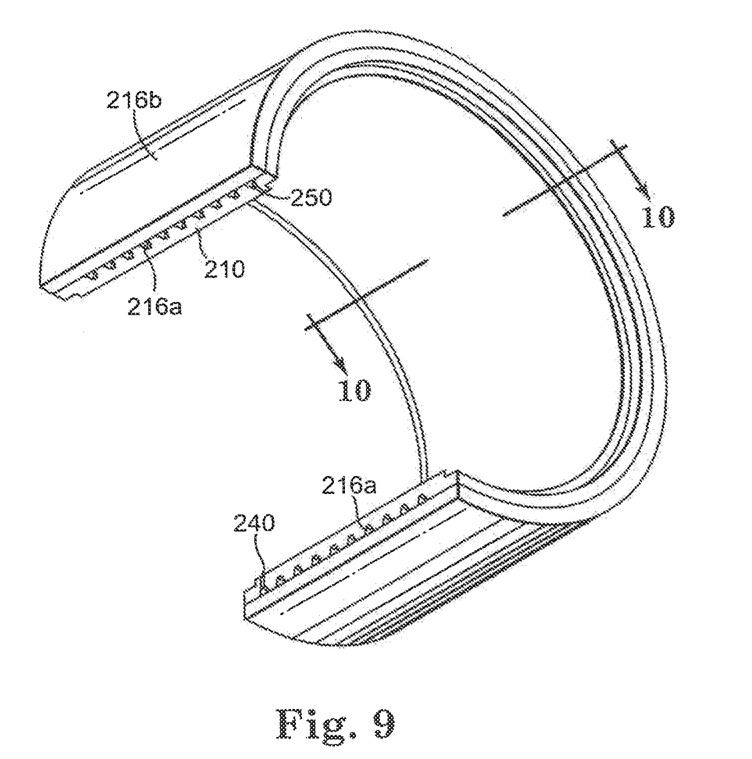
FIG. 9 is an assembled view of the combination shown in FIG. 8 with portions broken away.
Figure 10:
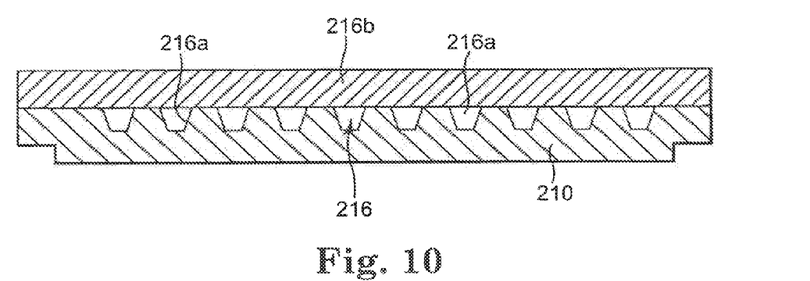
FIG. 10 is a cross-sectional view taken generally along the lines 10-10 in FIG. 9.
Figure 11:
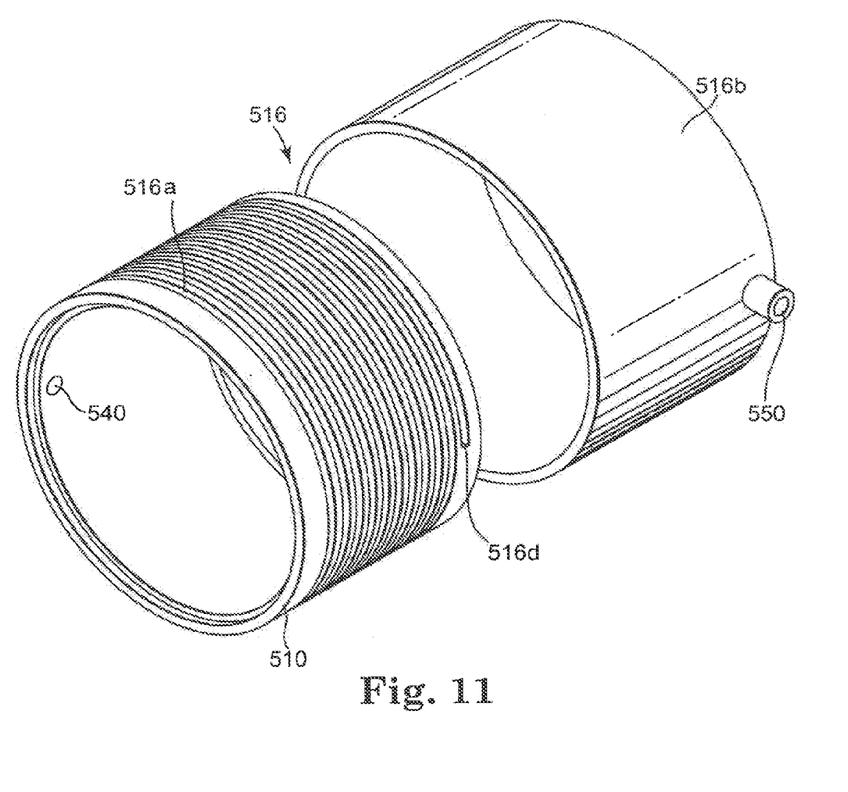
FIG. 11 is an exploded perspective view of another embodiment of a combination of a flow restrictor and regulator.
Figure 12:
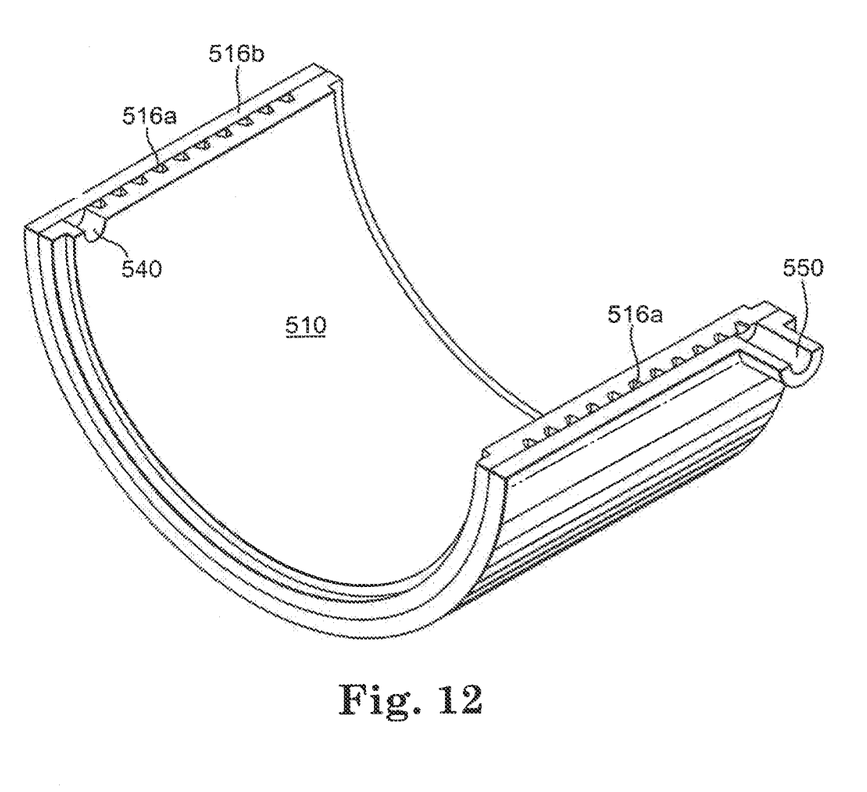
FIG. 12 is a cross-sectional view of the combination shown in FIG. 11, with the combination assembled.

The regulator 208 is in fluid communication with the drug reservoir 102 via line 109. The regulator 208 includes a housing 210. A flexible diaphragm 211 divides the chamber inside of the housing 210 into a first subchamber 212, which is a control chamber and a second subchamber 213, which is an outlet chamber. The diaphragm 211 may be any suitable flexible diaphragm and may be constructed from any suitable material such as silicone or titanium. A wall 214 further divides the chamber of the housing 210 into a third subchamber 215. The wall 214 has an opening 214a formed therein and provides a passageway to place the third subchamber 215 in fluid communication with subchamber 212. A flow restrictor or capillary 216 is placed in fluid communication between the first subchamber 212 and the second subchamber 213. The capillary 216 is a spiral machine groove 216a around the perimeter of the housing 210. An outer cylinder 216b has a friction fit around the spiral grooves 216a to form the capillary 216. The first end 216c of the capillary 216 is in fluid communication with the subchamber 212 through an opening 240 in the housing 210 and a second end 216d is in fluid communication with the second subchamber 213 through an opening 250 in the housing 210. FIGS. 8-10 show enlarged views of a portion of the housing 210 that incorporates the flow restrictor 216. It is understood that only that portion of the housing 210 that incorporates the spiral groove 216a is shown. A spiral groove 216a extends around the outer perimeter of the housing 210. A suitable cover or outer cylinder 216 is placed over the spiral grooves 216a and secured in place, such as with a friction fit. The flow restrictor is therefore an integral part of the housing of the regulator. The first end 216c is in fluid communication with the subchamber 212 through an opening 240 and the other end 216d of the capillary 216 is in fluid communication with the second subchamber 213 through an opening 250 formed in the housing 210. FIGS. 11 and 12 show another embodiment of a combination of the regulator and restrictor. The combination includes the housing 510 that incorporates the flow restrictor 516. A spiral groove 516a extends around the outer perimeter of the housing 510. A suitable cover or outer cylinder 516 is placed over the spiral grooves 516a and secured in place, such as with a friction fit. The flow restrictor is therefore an integral part of the housing of the regulator. The first end 516c is in fluid communication with the subchamber (not shown but similar to subchamber 212) through an opening 540 and the other end 516d of the capillary 516 is in fluid communication with the second subchamber (again not shown but similar to subchamber 213) through an opening 550. In this embodiment shown, the opening 550 does not go back into the subchamber. However, the opening 550 is later placed in fluid communication with the outlet (not shown but similar to 213b) by a suitable means such as a Y-type connection. It being understood that there are numerous ways that the capillary and regulator may be connected. The opening 214a is both an outlet for the third chamber 215 and an inlet for the first subchamber 112. An outlet 213b of the second subchamber 213 is adapted and configured to be in communication with a suitable outside device such as a catheter. A valve 217, positioned in opening 214a, is shown having a valve stem 217a and a sealing member 217b operatively connected to the stem 217a. As shown in FIG. 5, the valve stem 217 is connected to the diaphragm 211. Alternately, the valve would not necessarily have to be connected to the diaphragm and may be held in a closed position similar to that shown with respect to the embodiment shown in FIG. 3. In any event, the valve is operatively connected to the diaphragm 211, i.e., the movement of the diaphragm 211 will cause movement of the valve 217. As previously indicated, the valve 217 is normally closed. Further, without a pressure difference between the control chamber and the outlet chamber, the valve 217 is adjusted so that it is in an open position, as shown in FIG. 5. The valve stem 217 stays open until pressure in the first subchamber 212 exceeds pressure in the third subchamber 213 by a predetermined amount. For example, the valve 217 may be set to close when the control chamber or first subchamber 212 pressure is 2.0 psi greater than the second subchamber 213. At 2.0 psi, there will be a flow through the capillary 216 defined by the Hagen Poisielle laminar flow equations. The valves 21 will stabilize in a partially open position. If the valve 217 allows for more than the desired amount of drugs 105 to pass, then the pressure drop across the flow restrictor will increase, and this pressure change will tend to close the valve 217. If the valve 217 were to allow less than the desired amount of drugs 105 to pass, the pressure across the flow restrictor 216 will decrease, and the valve 217 will tend to open. This self-correcting phenomena will tend to keep the valve 217 positioned and flow rate at the desired amount. This flow rate may be maintained independent of temperature, altitude, bellows position and catheter resistance.

A spring 218 is positioned on top of the valve stem 217a and is positioned in the second subchamber 213. The housing 210 has a protrusion 210a which forms a cavity in which the spring 218 is positioned. This biasing spring 218 is used to set the initial open-closed pressure. Also, a spring 219 is positioned around the stem 217a in the first subchamber 212. A C-clip 220, or other suitable means, is operatively connected to the stem 217a. The spring 219 is positioned between the C-clip 220 and the wall 214, thereby providing an upward pressure, as viewed in FIG. 5, to close the valve 217.

Figure 6:
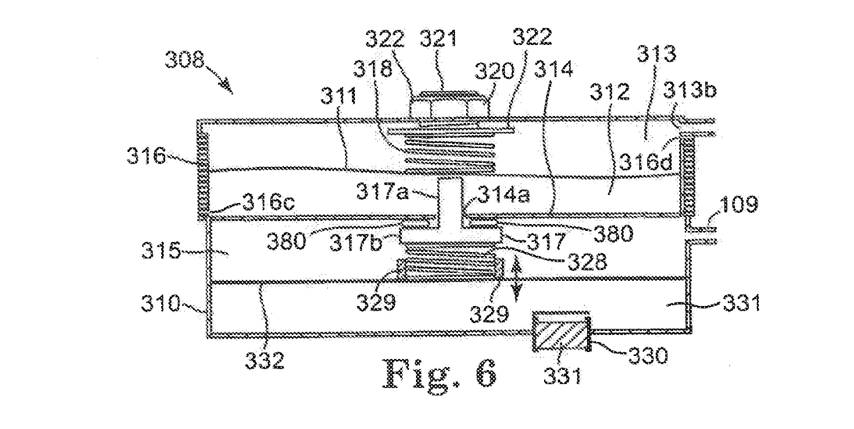
FIG. 6 shows another embodiment of a regulator for use in a drug delivery system shown in FIG. 4.

FIG. 6 is an example of a regulator 308 in which the springs, previously discussed with respect to FIG. 5, may be adjustable, and hence the flow rate adjustable. These could be controlled by electronics or telemetry or other methods known in the art. Two such examples are shown in FIG. 6.

The regulator 308 is in fluid communication with the drug reservoir 102. The line 109 places the reservoir 102 in fluid communication with the regulator 308. The regulator 308 includes a housing 310. A flexible diaphragm 311 divides the chamber inside of the housing 310 into a first subchamber 312, which is a control chamber and a second subchamber 313 which is an outlet chamber. The diaphragm 311 may be any suitable flexible diaphragm and may be constructed from any suitable materials such as silicone or titanium. A wall 314 further divides the chamber of the housing 310 into a third subchamber 315, an inlet chamber. The wall 314 has an opening 314a formed therein and provides a passageway to place the third subchamber 315 in fluid communication with subchamber 312. A flow restrictor, or capillary 316, similar to capillary 216, is placed in fluid communication between the first subchamber 312 and second subchamber 313. The first end 316a is in fluid communication with subchamber 312 and a second end 316d is in fluid communication with the second subchamber 313. The opening 314a is both an outlet for the third subchamber 315 and an inlet for the first subchamber 312. An outlet 313b of the second subchamber 313 is adapted and configured to be in communication with a suitable outside device such as a catheter. A valve 317, positioned in opening 314a, is shown having a valve stem 317a and a sealing member 317b operatively connected to the stem 317a. As shown in FIG. 6, the valve 317 is connected to the diaphragm 311. Alternately, the valve would not necessarily have to be connected to the diaphragm and may be held in a closed position similar to that shown with respect to the embodiment shown in FIG. 3. In any event, the valve is operatively connected to the diaphragm 311, i.e., movement of the diaphragm 311 will cause movement of the valve 317. As previously indicated, the valve 317 is normally closed. Further, without pressure difference between the control chamber and outlet chamber, the valve 317 is adjusted so that it is in an open position, as shown in FIG. 6. The valve 317 stays open until pressure in the first subchamber 312 exceeds the pressure in the second subchamber 313 by a predetermined amount, similar to that described with respect to FIG. 5. A spring 328 is positioned on the diaphragm 332 and under the sealing member 317b. The spring may be held in place by any suitable means, such as being positioned in a well formed by ring 329.

In addition, two ways of adjusting the flow rate are shown in FIG. 6. A biasing spring 318 is positioned in the second subchamber 313 and also positioned on the diaphragm 311 and above of the valve stem 317a. The amount of compression in the spring 318 is adjustable by an adjustable assembly 320. The adjustable assembly 320 includes a screw 321 that extends through the housing 310 and contacts the plate 322 that is in contact with and operatively connected to the spring 318. A nut 322 is positioned around the screw 321. As the nut 322 is rotated, the screw 321 will move up and down, thereby allowing the force exerted by the spring 318 to be adjustable.

There are a variety of ways to increase the pressure in the control chamber 312, but it is best to choose one which does not use energy to maintain a pressurized state. Some actuators like hydro-gels, or piezo-electrics, require power to maintain non-equilibrium conditions. Electrolysis will prevent maintaining new pressure states without applying power, except when changing pressure. The primary concerns with doing so includes corrosion, leakage, slow back reaction. However, with the present invention, back reaction time and leakage would not be an issue. With proper electrode selection, corrosion is also not an issue. Perhaps the simplest and lowest cost way to control pressure would be to use a septum access. A septum access 330 is provided in a fourth subchamber 331 that is defined by a diaphragm 332. The diaphragm 332 would preferably be thicker than the diaphragm 311. An access to the septum access 330 will allow the use of a needle diameter less than those used for refill and CAP access. A suitable septum 331 is placed in the septum access 330, as is well known in the art. A pressure sensor could be added for closed loop control, or monitoring during rate change.

Figure 7:
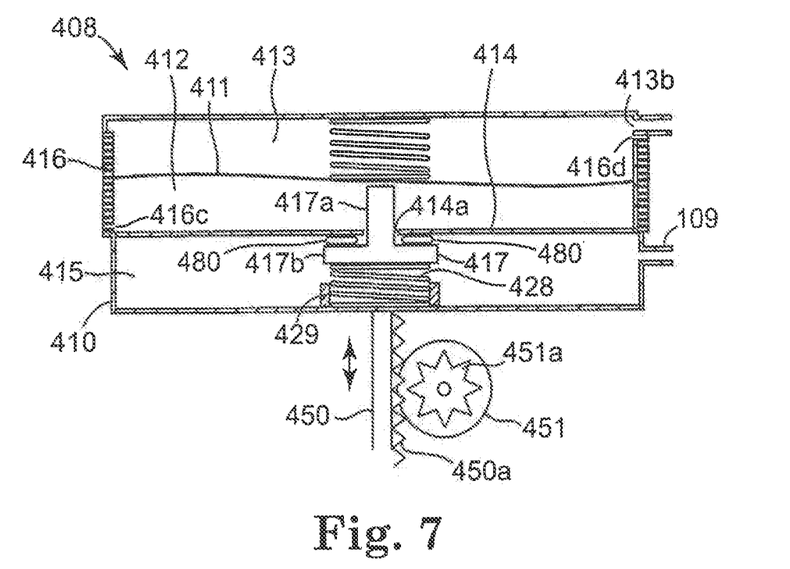
FIG. 7 shows another embodiment of a regulator for use in a drug delivery system shown in FIG. 4.

FIG. 7 shows an example of another embodiment of a regulator 408. The regulator 408 is similar in many respects to the regulator 308. However, the regulator 408 does not have an adjustable assembly 320 and utilizes a different method of adjusting the spring tension of spring 328. The regulator 408 is in fluid communication with the drug reservoir 102. The line 109 places the reservoir 102 in fluid communication with the regulator 408. The regulator 408 includes a housing 410. A flexible diaphragm 411 divides the chamber inside of the housing 410 into a first subchamber 412, which is a control chamber and a second subchamber 413 which is an outlet chamber. The diaphragm 411 may be any suitable flexible diaphragm and may be constructed from any suitable material such as silicone or titanium. A wall 414 further divides the chamber of the housing 410 into a third subchamber 415, an inlet chamber. The wall 414 has an opening 414a formed therein and provides a passageway to place the third subchamber 415 in fluid communication with the subchamber 412. A flow restrictor, or capillary 416, similar to capillary 216, is placed in fluid communication between the first subchamber 412 and the second subchamber 413. A first end 416c is in fluid communication with the subchamber 412 and a second end 416b is in fluid communication with the second subchamber 413. The opening 414a is both an outlet for the third subchamber 415 and an inlet for the first subchamber 412. An outlet 413b of the second subchamber 413 is adapted and configured to be in communication with a suitable outside device such as a catheter. A valve 417, positioned in opening 414a, is shown having a valve stem 417a and a sealing member 417b operatively connected to the stem 417a. As shown in FIG. 7, the valve 417 is connected to the diaphragm 411. Alternately, the valve would not necessarily have to be connected to the diaphragm and may be held in position similar to that shown with respect to an embodiment shown in FIG. 3. In any event, the valve is operatively connected to the diaphragm 411, i.e., movement of the diaphragm 411 will cause movement of the valve 417. As previously indicated, the valve 417 is normally closed. Further, without pressure difference between the control chamber and the outlet chamber, the valve 417 is adjusted so that it is in an open position, as shown in FIG. 7. The valve 417 stays open until pressure in the first subchamber 412 exceeds pressure in the second subchamber 413 by a predetermined amount, similar to that described with respect to FIG. 5. A spring 428 is positioned on the housing 410 and under the sealing member 417b. The spring 428 may be held in place by any suitable means such as being positioned in a well formed by a ring 429. The compression force of the spring 428 is adjusted by a rod 450 that extends through the housing 410 and can contact the spring 428. The rod 450 is moved up and down, as viewed in FIG. 7, by a motor 451. The motor 451 has a gear 451a that meshes with gears 450a that are operatively connected to the rod 450. Therefore, the rotation of the motor 451 causes linear movement of the rod 450. This linear movement thereby adjusts the compression force of the spring 428. This is just another example of how the compression force of the spring 428 may be adjusted, it being understood that other suitable means may also be utilized.

It should be noted that a seal 380 in FIG. 6 and a seal 480 in FIG. 7 is shown. It is understood that a metal on metal seal is usually not sufficient so that a seal 380, 480, made of a suitable compliant elastomer, is utilized between the sealing member 217b, 317b and the wall 214, 314. It is understood that a similar seal, while not shown, would also be utilized with regulators 19, 108 and 208.

Thus, embodiments of the Flow Regulator are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. A drug delivery system for implantation in a body for delivery of a liquid drug, the system comprising:
   a) a housing having a chamber;
   b) a diaphragm dividing the chamber into a first subchamber in a first flow path and a second subchamber in a second flow path;
   c) the diaphragm moveable in response to difference in pressure between the first subchamber and the second subchamber to regulate pressure difference between the first flow path and the second flow path;
   d) a valve operatively linked with the diaphragm to open the first flow path when pressure in the second flow path exceeds pressure in the first flow path by a predetermined amount;
   e) a pump having an inlet in fluid communication with the first flow path and an outlet in fluid communication with the second flow path;
   f) an infusion pump housing defining a drug reservoir;
   g) a propellant chamber within the pump housing and proximate the drug reservoir, wherein pressure is exerted on the drug reservoir; and
   h) the drug reservoir having a reservoir inlet for receiving the liquid drug and a reservoir outlet, the outlet in fluid communication with the first flow path, whereby the liquid drug is delivered independent of changes in reservoir pressure and ambient pressure.

2. An implantable flow regulator for use with a drug delivery system, the flow regulator comprising:
   a) a chamber;
   b) a diaphragm dividing the chamber into a first subchamber and a second subchamber;
   c) a third subchamber in fluid communication with the first subchamber through a first inlet;
   d) a valve operatively connected to the diaphragm, the valve for controlling flow from the third subchamber to the first subchamber through the first inlet, wherein pressure differences between the first subchamber and the second subchamber result in movement of the diaphragm and the movement of the diaphragm controls operation of the valve;
   e) the first subchamber having a first outlet and the second subchamber having a second inlet and a second outlet; and
   f) a flow restrictor having a first end in fluid communication with the first outlet and a second end in fluid communication with the second inlet, wherein flow of a drug from a drug delivery system through the second outlet is regulated.

3. The implantable flow regulator of claim 2, wherein the valve is a normally closed valve and is open when there is no pressure differential across the diaphragm.

4. The implantable flow regulator of claim 3, wherein the diaphragm is constructed from titanium.

5. The regulator of claim 2, further comprising:
   a) the chamber having an outer surface;
   b) the flow restrictor comprising a spiral groove operatively connected to the outer surface and an outer cylinder positioned over the spiral groove, wherein a capillary is formed by the groove and outer cylinder.

6. The regulator of claim 5, wherein the spiral groove is formed in the outer housing.

7. The regulator of claim 6, wherein the outer cylinder has a friction fit over the spiral groove.

8. The regulator of claim 2, further comprising a biasing member positioned on the diaphragm in the second subchamber and over the valve, whereby an opening pressure to open the valve is effected.

9. A drug delivery system comprising:
a) the implantable flow regulator of claim 2;
b) a valve biasing spring;
c) an actuator rod extending into the third subchamber and positioned to compress the valve biasing spring; and
d) a motor operatively connected to the rod, thereby controlling flow rate of the drug.

10. A drug delivery system for implantation in a body for delivery of a liquid drug, the system comprising:
a) a chamber;
b) a diaphragm dividing the chamber into a first subchamber and a second subchamber;
c) a third subchamber in fluid communication with the first subchamber through a first inlet;
d) a valve operatively connected to the diaphragm, the valve for controlling flow from the third subchamber to the first subchamber through the first inlet, wherein pressure differences between the first subchamber and the second subchamber result in movement of the diaphragm and the movement of the diaphragm controls operation of the valve;
e) the first subchamber having a first outlet and the second subchamber having a second inlet and a second outlet; and
f) an infusion pump housing defining a drug reservoir;
g) a propellant chamber within the pump housing and proximate the drug reservoir, wherein pressure is exerted on the drug reservoir;
h) the drug reservoir having a reservoir inlet for receiving a drug and a reservoir outlet, the reservoir outlet in fluid communication with the first inlet of the first subchamber; and
i) a flow restrictor having a first end in fluid communication with the first outlet and a second end in fluid communication with the second inlet, wherein flow of a drug from a drug delivery system through the second outlet is regulated.

11. The drug delivery system of claim 10, the valve is a normally closed valve and is open when there is no pressure differential across the diaphragm.

12. The drug delivery system of claim 11, wherein the diaphragm is constructed from titanium.

13. The drug delivery system of claim 10, further comprising:
a) a fourth subchamber;
b) a second diaphragm between the third and fourth subchambers;
c) a valve biasing spring carried by the second diaphragm; and
d) the fourth subchamber having a volume of fluid that is changeable, thereby moving the diaphragm and changing spring force on the valve biasing spring.

14. The drug delivery system of claim 13, further comprising a septum operably connected to the fourth subchamber, wherein the volume of fluid in the fourth subchamber is changeable through the septum by a syringe.

15. The drug delivery system of claim 10, further comprising:
a) the chamber having an outer surface;
b) the flow restrictor comprising a spiral groove operatively connected to the outer surface and an outer cylinder positioned over the spiral groove, wherein a capillary is formed by the groove and outer cylinder.

16. The drug delivery system of claim 15, wherein the spiral groove is formed in the outer housing.

17. The drug delivery system of claim 16, wherein the outer cylinder has a friction fit over the spiral groove.

18. The drug delivery system of claim 10, further comprising a biasing member positioned on the diaphragm in the second subchamber and over the valve, whereby an opening pressure to open the valve is effected.

19. An implantable flow regulator and flow restrictor combination for use with a drug delivery system, comprising:
a) a chamber;
b) a diaphragm dividing the chamber into a first subchamber and a second subchamber;
c) a third subchamber in fluid communication with the first subchamber through a first inlet;
d) a valve operatively connected to the diaphragm, the valve for controlling flow from the third subchamber to the first subchamber through the first inlet, wherein pressure differences between the first subchamber and the second subchamber result in movement of the diaphragm and the movement of the diaphragm controls operation of the valve;
e) the first subchamber having a first outlet and the second subchamber having a second inlet and a second outlet;
f) the chamber having an outer surface; and
g) a flow restrictor comprising a spiral groove operatively connected to the outer surface and an outer cylinder positioned over the spiral groove, wherein a capillary is formed by the spiral groove and outer cylinder.

* * * * *